United States Patent [19]

Moore

[11] Patent Number: Plant 5,975

[45] Date of Patent: May 12, 1987

[54] ROSE PLANT NAMED 'MORCHARI'

[75] Inventor: Ralph S. Moore, Visalia, Calif.

[73] Assignee: Sequoia Nursery, Visalia, Calif.

[21] Appl. No.: 765,827

[22] Filed: Aug. 15, 1985

[51] Int. Cl.[4] ..... A01H 5/00

[52] U.S. Cl. ..... Plt./5

[58] Field of Search ..... Plt./5

*Primary Examiner*—James R. Feyrer

[57] ABSTRACT

This invention relates to a new and distinct variety of miniature rose plant primarily identified by small, very double lavender to pink lavender flowers and the unique spreading habit of growth.

2 Drawing Figures

The present invention relates to a new and distinct variety of hardy, dwarf, bush type rose plant of the miniature class; the variety being primarily characterized — as to novelty — by the fragrant very double flowers and the unique coloring which may vary from pink to lavender and at times quite purple.

The variety is further characterized by:

an abundance of bloom, with flowers usually borne several to the stem in small clusters of 5 to 15.

Very fragrant.

A plant which is moderately vigorous, of rounded, spreading shape with small matt foliage with pointed leaflets; the buds and flowers being similar in form to Snow Magic (miniature — not patented).

The plant, which has a normal height of 10–12 inches can easily be maintained at lesser height by occasional trimming.

A plant which grows and blooms satisfactorily both in greenhouse and outdoors; is good for growing in pots, or tubs and provides excellent garden decoration. Not good for cutting.

The present variety of miniature rose was originated by me at Sequoia Nursery located at Visalia, Calif., under conditions of careful control and observation, as a cross between Little Chief (miniature — not patented) as the seed parent and Violette (Rambler — not patented) as the pollen parent.

Subsequent to origination of the variety I successfully asexually reproduced it at Sequoia Nursery, located as aforesaid, by budding as well as by cuttings; the reproductions having run true in all respects.

The color photographs illustrate the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; spreading; seedling; greenhouse; outdoors; garden decoration; hanging plant.

Class: miniature. Variety identification: Morchari (Commercial synonym: Sweet Chariot).

Flowers borne: Several together (5–15) on slender wirey stems.

Quantity of bloom: Abundant both outside and in greenhouse.

Bud:

*Peduncle.*—Medium length; slender; medium green, sometimes tinted bronze (outdoors); with no short hairs.

*Before calyx breaks, size.*—Small.

*Form.*—Ovoid to pointed with several small foliaceous apendages and few or no short hairs on surface of bud; with foliaceous parts extending beyond the tip of the bud equal to one-half or more of its length.

*Color.*—Medium green, occasionally tinted with bronze (outdoors).

*As calyx breaks, color.*—Medium shade of lavender pink.

*Opening.*—Opens well in all weather.

Bloom:

*Size when fully open.*—Small, averaging about 35 mm ($1\frac{3}{8}''$).

*Petalage.*—Double — averaging about 55–60 petals, arranged regularly plus an occasional petaloid.

*Form.*—Cupped at first then becoming more rounded. Open flowers usually have few or no stamens.

Petals: Fairly thin; satiny on inside and on outside surface.

*Shape.*—Outside petals, broad lanceolate with rounded tip; intermediate — lanceolate with very short acute tip; inside — lanceolate with acute tip.

Color: Newly opened flower from a plant grown in plastic greenhouse (July 1985), Visalia, Calif.

*Outside petal.*—Outside surface — white at base then gradually blending to near Lilac Purple 031/1 at tip/petal from another flower may be near white at base and blending to near Fuchsia Purple 28/1 or near Rhodamine Purple 29/2 at tip. Inside surface — white at base blending to near Rhodamine Purple 29/1 or near Fuchsia Purple 28 or Lilac Purple 031/1 at tip. (Flower color of this variety often varies from flower to flower — color often depends on weather and light exposure).

*Intermediate petal.*—Outside surface — similar to outside petal. Inside surface similar to outside petal.

*Inner petal.*—Outside surface — similar to intermediate petal; inside surface — similar to intermediate petal. General color effect; newly opened flowers — color — lavender — lilac — pink. Three days open — color similar to fresh open flowers — often flower color begins light pinkish lavender becoming more lilac or purple with age. Behavior — opens well in all weather. Spent petals or flowers drop off. Flower longevity (July–August 1985) plant in pot 5–6 days or longer. Cut flowers: this variety does not keep as a cut flower.

Reproductive organs:

*Stamens.*—Few, usually none.

*Pollen.*—Little or none.

*Pistils.*—Average number.

*Styles.*—Varying length; pinkish-lavender, bunched.

*Ovaries.*—All enclosed in calyx.

*Hips.*—Few or none.

*Sepals.*—Permanent; spear shaped; recurved.

*Seed.*—Few — usually none.

Foliage:

*Leaves.*—Compound of five (sometimes three or seven) leaflets; small; leathery; matt.

*Leaflets.*—Shape: broad, lanceolate; apex acute; base — rounded.

*Color.*—Medium green; new growth — normal (medium) green (sometimes tinted reddish).

*Rachis.*—Medium strength; upper side usually smooth with no hairs; grooved; underside may have 2 or 3 small thorns (or claws) and few or no short prickles.

*Stipules.*—Medium to short length; medium width; medium to short length narrow points which turn out usually at about 45 degrees or less.

Growth:

*Habit.*—Dwarf; bushy; spreading; much branched.

*Growth.*—Moderately vigorous; internodes short.

*Canes.*—Medium; slender; sturdy.

*Main stems.*—Color: medium green.

*Thorns.*—Several — usually quite short — curved to straight; color — brown.

*Hairs.*—Few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, spreading, much branched habit, substantially as illustrated and described, characterized by buds and flowers of varying shades of lilac, purple and pinkish lavender, the bud being pointed in the early opening stage with the full open flower being rounded to slightly cupped with 55–60 petals; and further characterized by a plant of compact, vigorous, well rounded shape, the said plant being easy to propagate from soft wood cuttings, with an abundance of small matt foliage, the flowers being very fragrant and borne usually in clusters of 5 to 15 or more.

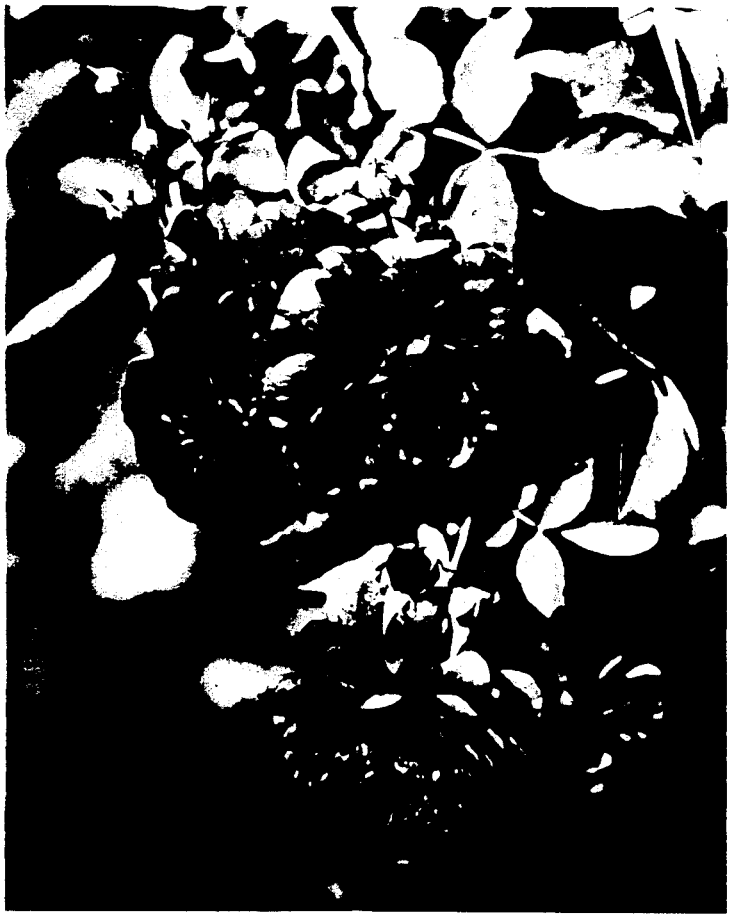
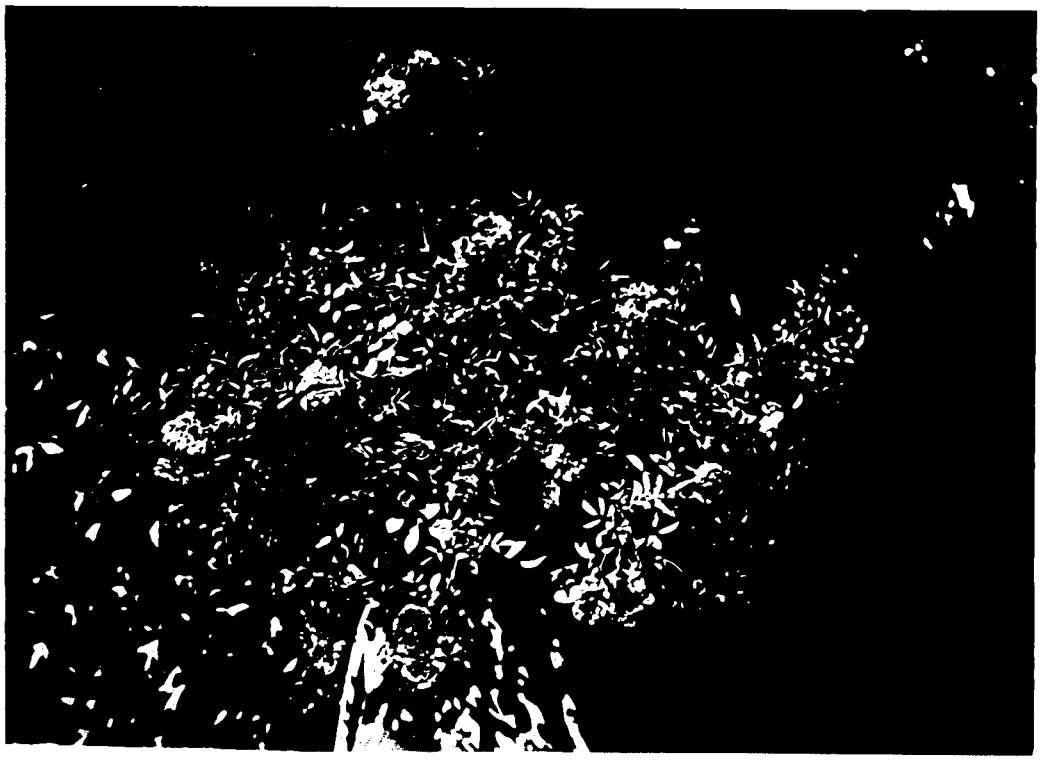

* * * * *